(12) United States Patent
Sato et al.

(10) Patent No.: US 10,716,314 B2
(45) Date of Patent: Jul. 21, 2020

(54) YOGURT PRODUCT AND METHOD FOR MANUFACTURING SAME

(71) Applicant: Godo Shusei Co., Ltd., Tokyo (JP)

(72) Inventors: Tomoko Sato, Chiba (JP); Jun Yoshikawa, Chiba (JP)

(73) Assignee: GODO SHUSEI CO., LTD., Tokyo (JP)

( * ) Notice: Subject to any disclaimer, the term of this patent is extended or adjusted under 35 U.S.C. 154(b) by 51 days.

(21) Appl. No.: 16/062,475

(22) PCT Filed: Dec. 15, 2016

(86) PCT No.: PCT/JP2016/087327
§ 371 (c)(1),
(2) Date: Jun. 14, 2018

(87) PCT Pub. No.: WO2017/104729
PCT Pub. Date: Jun. 22, 2017

(65) Prior Publication Data
US 2018/0368429 A1    Dec. 27, 2018

(30) Foreign Application Priority Data
Dec. 16, 2015   (JP) ................................. 2015-244855

(51) Int. Cl.
*A23C 9/127*    (2006.01)
*A23L 29/00*    (2016.01)
(Continued)

(52) U.S. Cl.
CPC ............ *A23C 9/1275* (2013.01); *A23L 29/06* (2016.08); *C12P 1/00* (2013.01); *A23Y 2220/15* (2013.01);
(Continued)

(58) Field of Classification Search
CPC .......................... A23C 9/1275; A23Y 2240/75
See application file for complete search history.

(56) References Cited

U.S. PATENT DOCUMENTS

| 3,661,594 A | 5/1972 | Imai et al. |
| 2004/0091576 A1 | 5/2004 | Miyashita |

(Continued)

FOREIGN PATENT DOCUMENTS

| CN | 104673773 A | 6/2015 |
| EP | 0610649 A1 | 8/1994 |

(Continued)

OTHER PUBLICATIONS

Milk Facts. No date provided. http://milkfacts.info/Milk%20Composition/Milk%20Composition%20Page.htm.*

(Continued)

*Primary Examiner* — Anthony J Weier
(74) *Attorney, Agent, or Firm* — Osha Liang LLP (57) ABSTRACT

Provided is a method for manufacturing a fermented milk product, including sequentially performing a first step of mixing raw material milk and lactic acid bacteria to obtain a mixed liquid, and a second step of fermenting the mixed liquid, characterized by performing a step of adding a *Paenibacillus*-derived protease to the raw material milk and/or the mixed liquid (protease addition step) before the second step is completed. According to this manufacturing method, the hardness of the fermented milk product can be adjusted to a desired value while original smoothness of the fermented milk product is maintained.

13 Claims, 6 Drawing Sheets

(51) Int. Cl.
  *C12P 1/00* (2006.01)
  *C12N 9/52* (2006.01)
(52) U.S. Cl.
  CPC ....... *A23Y 2220/17* (2013.01); *A23Y 2220/63* (2013.01); *A23Y 2240/75* (2013.01); *C12N 9/52* (2013.01)

(56) References Cited

U.S. PATENT DOCUMENTS

| | | | |
|---|---|---|---|
| 2005/0095316 | A1 | 5/2005 | De Greeftrial et al. |
| 2005/0095317 | A1 | 5/2005 | Queguiner et al. |
| 2006/0099317 | A1 | 5/2006 | Yasokawa et al. |
| 2007/0166447 | A1 | 7/2007 | Ur-Rehman et al. |
| 2009/0297660 | A1* | 12/2009 | Silver ............... A23C 19/0328 426/36 |
| 2017/0367360 | A1* | 12/2017 | Yu ..................... A23C 9/1209 |
| 2018/0042253 | A1 | 2/2018 | Eisele et al. |

FOREIGN PATENT DOCUMENTS

| | | |
|---|---|---|
| EP | 0642740 A1 | 3/1995 |
| EP | 896509 A1 | 2/1999 |
| EP | 1535999 A1 | 6/2005 |
| FR | 1569837 A | 6/1969 |
| JP | S44-27714 B1 | 11/1969 |
| JP | H06-197688 A | 7/1994 |
| JP | H06-276933 A | 10/1994 |
| JP | H07-147898 A | 6/1995 |
| JP | 3145829 B2 | 3/2001 |
| JP | 3182954 B2 | 7/2001 |
| JP | 2002-306063 A | 10/2002 |
| JP | 2004-033093 A | 2/2004 |
| JP | 2004-180553 A | 7/2004 |
| JP | 2005-521391 A | 7/2005 |
| JP | 2008-283948 A | 11/2008 |
| JP | 2010-512798 A | 4/2010 |
| SU | 471380 A1 | 5/1975 |
| WO | 97/38587 A1 | 10/1997 |
| WO | 03070009 A1 | 8/2003 |
| WO | 2013/039188 A1 | 3/2013 |
| WO | 2016/164096 A1 | 10/2016 |

OTHER PUBLICATIONS

International Preliminary Report on Patentability issued in International Application No. PCT/JP2016/087327; dated Jun. 28, 2018 (11 pages).
International Search Report issued in PCT/JP2016/087327 dated Mar. 7, 2017 (7 pages).
Written Opinion of the International Searching Authority issued in PCT/JP2016/087327 dated Mar. 7, 2017 (7 pages).
Edited by Shuichi Uenogawa, Nyu no Kagaku, 3rd print, Mar. 25, 1998 (Mar. 25, 1998), p. 19 (3 pages).
Supervised by Yoshiko Kagawa, Shokuhin Seibunhyo 2014, 1st edition, 1st print, Feb. 10, 2014 (Feb. 10, 2014), p. 200 to 201 (3 pages).
Hosseini, H. et al.; "Isolation, identification and monitoring of contaminant bacteria in Iranian Kefir type drink by 16S rDNA sequencing"; Food Control, 2012, vol. 25, No. 2, pp. 784-788 (5 pages).
Alvarez, V.M. et al.; "Influence of growth conditions on the production of extracellular proteolytic enzymes in Paenibacillus peoriae NRRL BD-62 and Paenibacillus polymyxa SCE2"; Letters in Applied Microbiology, 2006, vol. 43, No. 6, pp. 625-630 (6 pages).
Hirokawa, K. et al.; "An enzymatic method for the determination of hemoglobinA(1C)"; Biotechnology Letters, 2005, vol. 27, No. 14, pp. 963-968 (6 pages).
Hang, F.; "High Milk-Clotting Activity Expressed by the Newly Isolated *Paenibacillus* spp. Strain BD3526"; Molecules, Jan. 2016, vol. 21, No. 1, 73 (14 pages).
"Paenibacillus bovis," Literature reference Int. J. Syst. Evol. Microbiol. Int. J. Syst. Evol. Microbiol; Apr. 17, 2019, pp. 1-7, XP055582150 (7 pages).
H. Seiler,. "Foto-Bibliothek für lebensmittelassoziierte aerobe Sporenbildner," Oct. 1, 2010, XP055581263 (317 pages).
Extended European Search Report issued in corresponding European Application No. 16875706.0; dated May 21, 2019 (9 pages).

* cited by examiner

YOGURT PRODUCT AND METHOD FOR MANUFACTURING SAME

TECHNICAL FIELD

The present application claims priority based on Japanese Patent Application No. 2015-244855 filed on Dec. 16, 2015, all the contents of which are incorporated herein by reference. The present invention relates to a fermented milk product and a method for manufacturing the same.

BACKGROUND ART

Fermented milk is roughly classified into two types. One is a pre-fermentation type, obtained by fermenting raw material milk in a large-sized manufacturing tank, crushing the obtained fermented milk, and then packing the fermented milk in an individual food container. The other is a post-fermentation type, obtained by packing raw material milk, lactic acid bacteria, and the like in an individual food container and then fermenting the milk. In any type, the fermented milk packed and fermented in an individual food container is delivered to a final consumer on a distribution route.

Conventionally, on a distribution route, fermented milk in an individual food container may be broken disadvantageously, or in a case of fermented milk containing a fruit pulp, the fruit pulp may sink into a bottom of an individual food container disadvantageously. Examples of a method for preventing these problems include a method for adding a gelling agent such as agar or gelatin to fermented milk to increase the hardness of the fermented milk. However, by adding the gelling agent, fermented milk is hardly broken, but on the other hand, an original smooth texture of the fermented milk is lost disadvantageously.

In order to solve the above problem, a method for adding an enzyme in manufacturing fermented milk has been proposed (for example, see Patent Literatures 1 and 2). Patent Literature 1 discloses a method using peroxidase, and Patent Literature 2 discloses a method using transglutaminase.

CITATION LIST

Patent Literature

Patent Literature 1: JP 3145829 B2
Patent Literature 2: JP 3182954 B2

SUMMARY OF INVENTION

Technical Problem

Patent Literature 1 describes that manufacturing fermented milk by adding peroxidase improves smoothness and water retention and reduces hardness.

Patent Literature 2 discloses that in manufacturing fermented milk by adding transglutaminase, an enzyme action of the transglutaminase forms an (intermolecular and intramolecular) network between milk proteins and in milk protein (gelation). Patent Literature 2 does not describe the hardness of the fermented milk obtained. However, it is presumed from a mechanism of the action of the transglutaminase that the hardness of the fermented milk increases.

According to the invention of Patent Literature 1 or 2, it is expected that the hardness of the fermented milk is decreased or increased. However, none of enzymes only decreases or increases the hardness of the fermented milk. According to a conventional technology, it is difficult to adjust the hardness of fermented milk to a desired value by a single enzyme while the original smoothness of the fermented milk is maintained.

Therefore, an object of the present invention is to provide a method for manufacturing a fermented milk product capable of adjusting the hardness of the fermented milk product to a desired value while the original smoothness of the fermented milk product is maintained.

Solution to Problem

The present inventors have found that by adding a specific protease to milk and fermenting the milk, the hardness of a curd of a fermented milk product can be adjusted and that the inside thereof becomes more uniform and smooth, and thus have completed the present invention.

Therefore, the present invention provides:

[1] a method for manufacturing a fermented milk product, including sequentially performing a first step of mixing raw material milk and lactic acid bacteria to obtain a mixed liquid and a second step of fermenting the mixed liquid, and performing a step of adding a protease derived from the genus *Paenibacillus* to the raw material milk and/or the mixed liquid (protease addition step) before the second step is completed;

[2] the method for manufacturing a fermented milk product according to [1], in which a ratio between the milk fat content (% by mass) contained in the raw material milk and the addition amount (PU/g) of the protease (the milk fat content: the addition amount of the protease) is 50:1 to 1:10;

[3] the method for manufacturing a fermented milk product according to [1] or [2], in which the addition amount of the protease is 0.05 to 10.0 PU/g based on the total mass of the raw material milk;

[4] the method for manufacturing a fermented milk product according to [1], in which the milk fat content contained in the raw material milk is 0 to 10% by mass;

[5] the method for manufacturing a fermented milk product according to any one of [1] to [4], in which the nonfat milk solid content contained in the raw material milk is 3.0 to 20% by mass;

[6] the method for manufacturing a fermented milk product according to any one of [1] to [5], in which the protease has the following properties (1) to (5), (1) the protease is produced by bacteria belonging to *Paenibacillus*, (2) the protease degrades κ-casein and hemoglobin in a neutral pH range, (3) the protease is stable at a pH of 5.5 to 9.0 and has an optimum pH of 7.0 to 8.0, (4) the protease acts at 20 to 75° C. and has an optimum temperature of 50 to 60° C., and (5) the protease is estimated to have a molecular weight by SDS polyacrylamide gel electrophoresis of 32,000 to 34,000 Da;

[7] the method for manufacturing a fermented milk product according to any one of [1] to [6], further including performing a step of adding one or more selected from lactase, glucose isomerase, glucose oxidase, transglutaminase, lipase, cellulase, amylase, inulinase, laccase, peroxidase, and a protease other than the above-described protease to the raw material milk and/or the mixed liquid;

[8] a fermented milk product containing a *Paenibacillus*-derived protease, in which
a breaking point of a curd as measured using a creep meter is 0.002 to 1.0 N; and

[9] a method for manufacturing a fermented milk product, including:

a first step of mixing raw material milk and lactic acid bacteria to obtain a mixed liquid;

a second step of fermenting the mixed liquid; and a step of adding a *Paenibacillus*-derived protease to the raw material milk and/or the mixed liquid (protease addition step) before the completion of the second step, in which using a desired hardness of a curd of the fermented milk product, the milk fat content contained in the raw material milk, and the addition amount of the *Paenibacillus*-derived protease as indices, the milk fat content and the addition amount of the protease are determined, and the fermentation step is performed.

Advantageous Effects of Invention

According to the present invention, it is possible to provide a fermented milk product capable of adjusting the hardness of the fermented milk product to a desired value and maintaining the original smoothness of the fermented milk product, and a method for manufacturing the fermented milk product.

BRIEF DESCRIPTION OF DRAWINGS

Panel A of FIG. 1 is a graph showing results of break strength analysis by a creep meter for yoghurts of Manufacture Examples 1 and 5, and Panel B of FIG. 1 is a graph showing results of break strength analysis by a creep meter for yoghurts of Manufacture Examples 2 and 6.

Panel A of FIG. 2 is a graph showing results of texture analysis by a creep meter for yoghurts of Manufacture Examples 1 and 5, and Panel B of FIG. 2 is a graph showing results of texture analysis by a creep meter for yoghurts of Manufacture Examples 2 and 6.

DESCRIPTION OF EMBODIMENTS

A method for manufacturing a fermented milk product according to the present invention essentially uses a *Paenibacillus*-derived protease, a lactic acid bacteria starter, and raw material milk, and optionally uses an additive such as a stabilizer. Hereinafter, explanation will be made in the order of (1) raw materials of a fermented milk product, (2) addition amounts thereof, (3) properties of a fermented milk product, (4) a method for manufacturing a fermented milk product, and (5) applications.

<<Raw Materials of Fermented Milk Product>>

<Neutral Protease>

A protease that can be preferably used in the present invention may have the following properties.

(1) the protease may be produced by bacteria belonging to *Paenibacillus*, (2) the protease may degrade κ-casein and hemoglobin in a neutral pH range, (3) the protease may have an optimum pH of 7.0 to 8.0, (4) the protease may be a neutral protease stable at a pH of 5.5 to 9.0, (5) the protease may act at 20 to 75° C. and may have an optimum temperature of 55° C., and (6) the protease may be estimated to have a molecular weight by electrophoresis of 32,000 to 34,000 Da.

*Paenibacillus* was classified as *Bacillus* in the past but has been recently reclassified and proposed as a new genus. A protease having the above properties can be obtained from other species including *Paenibacillus polymyxa* re-identified from *Bacillus polymyxa* and *Paenibacillus* sp. Some literatures and the like use a term of *Bacillus polymyxa*, but *Bacillus polymyxa* is synonymous therewith.

The protease which can be used in the present invention may have the following properties in detail.

(a) Action

The protease may exhibit general properties as a neutral protease. And the protease may degrade a protein such as casein or hemoglobin in a neutral pH range to produce a peptide or a free amino acid.

It may have been confirmed that the protease cuts 12 peptide bonds of Pha(1)-Val(2), His(5)-Leu(6), His(10)-Leu (11), Glu(13)-Ala(14), Ala(14)-Ler(15), Ler(15)-Tyr(16), Tyr(16)-Leu(17), Leu(17)-Val(18), Gly(23)-Phe(24), Phe (24)-Phe(25), Phe(25)-Tyr(26), and Lys(29)-Ala(30) with respect to a B chain of an oxidized insulin.

(b) Substrate Specificity

The protease may exhibit a mild proteolytic action on κ-casein in a neutral pH range. The protease may hardly exhibit a proteolytic action on α-casein or β-casein in a neutral pH range.

(c) Optimum pH and Stable pH Range i) Optimum pH: An optimum pH for a proteolytic action on κ-casein may be 7.0 to 8.0.

ii) Stable pH range: The protease may be highly stable in a range of 5.5 to 9.0.

(d) Range of Preferable Action Temperature

The protease may act in a range of 20° C. to 75° C. And the protease may have an optimum temperature of 50 to 60° C. The most preferable temperature may be 55° C.

(e) Conditions for Inactivation by pH, Temperature, and the Like

At a pH of 3.0 or less and a pH of 10.0 or more, activity may be completely lost. In addition, the protease may be completely inactivated by a heat treatment at 65° C. for 10 minutes.

(f) Inhibition, Activation, and Stabilization

The protease may be inhibited by a metal chelating agent such as ethylenediamine tetraacetate (EDTA), citric acid, o-phenanthroline, 2,2-dipyridyl, or sodium fluoride, and an oxidizing agent such as N-bromosuccinimide (NBS) or iodine.

The protease may be stabilized by a calcium ion and may need a zinc ion for its activity.

(g) Molecular Weight

The protease may be estimated to have a molecular weight by electrophoresis of 32,000 to 34,000 Da.

A protease is classified into the following five types depending on a catalytic site thereof. These are an acidic protease (catalytic site: aspartic acid, example: pepsin), a metalloprotease (catalytic site: metal), a serine protease (catalytic site: serine, example: trypsin), a cysteine protease (catalytic site: amino acid having an SH group, such as cysteine, example: papain), and a mixed type having at least two of these types (example: actinase AS). The *Paenibacillus*-derived protease used in the present invention may belong to a neutral metalloprotease. As described below, a neutral protease may be inactivated due to reduction in pH of milk by fermentation. Therefore, a protease may be inactivated in a milk product according to the present invention.

The protease in the present invention may be an endo type neutral metalloprotease. The endo type protease has a function of roughly degrading a protein and lowering a molecular weight thereof. If a protease acts on a milk protein, bitterness is exhibited in many cases. However, even if the protease of the present invention acts on a milk protein, bitterness is not exhibited, taste or odor is not affected.

κ-casein (kappa casein) as a component of milk casein plays an important role in forming a casein micelle. The protease may specifically degrade this κ-casein without largely changing structures of other casein proteins. This result in improving the texture (smoothness) of an obtained fermented milk product.

(Type of Raw Material Organism)

A protease may be isolated from a very wide range of organisms including microorganisms. A preferable protease is derived from microorganisms from viewpoints of price and reactivity. Examples of such a protease include proteases derived from microorganisms belonging to *Bacillus* or *Paenibacillus*, *Geobacillus*, *Aspergillus*, *Rhizopus*, *Rhizomucor*, and *Streptomyces*, and a protease derived from lactic acid bacteria. The protease that can be used as an enzyme in the present invention is derived from *Paenibacillus*. Specifically, the protease is preferably derived from microorganisms (bacteria) selected from the group consisting of *Paenibacillus polymyxa*, *Paenibacillus macerans*, *Paenibacillus pabuli*, *Paenibacillus peoriae*, *Paenibacillus thiaminolyticus*, *Paenibacillus validus*, *Paenibacillus glucanolyticus*, *Paenibacillus kobensis*, *Paenibacillus lautus*, *Paenibacillus alginolyticus*, *Paenibacillus alvei*, *Paenibacillus amylolyticus*, *Paenibacillus chitinolyticus*, *Paenibacillus chondroitinus*, *Paenibacillus curdlanolyticus*, *Paenibacillus durus*, *Paenibacillus ehimensis*, and *Paenibacillus* sp.

The enzyme may be in any form such as a purified enzyme, a semi-purified enzyme, a crude enzyme, or a disrupted bacterial cell (preferably a freeze-dried product) as long as it has a κ-casein degrading action. However, because many proteases that can degrade κ-casein are liable to exhibit bitterness and off-taste, the enzyme is preferably a metalloprotease having the above-described properties, derived from microorganisms (bacteria) belonging to *Paenibacillus*, particularly *Paenibacillus polymyxa* or *Paenibacillus* in which homology of 16S rDNA is 98% or more as compared with the sequence of *Paenibacillus polymyxa*. When metalloproteases derived from these genera are added to milk, they have an action of degrading κ-casein contained in milk and do not cause bitterness or off-taste in processed milk.

A preferable metalloprotease in the present invention may have a residual activity of 10% or less when being reacted for one hour at a pH of 4.5 using azocasein as a substrate at 43° C., which is a general fermentation temperature for a fermented milk product. By virtue of this property, the protease activity does not remain in a fermentation preparation, and it is possible to prevent the protease from adversely affecting the fermentation preparation during storage.

(Method for Manufacturing Metalloprotease)

The metalloprotease used in the present invention can be collected from microorganisms and purified by a conventional general method. Therefore, the protease can be manufactured by genetic recombination or non-genetic recombination. For example, a *Paenibacillus polymyxa* NBRC 15309 strain is cultured in a Nutrient medium manufactured by Difco Laboratories Inc. or the like and filtered or centrifuged from the culture to obtain the protease as a culture supernatant. In addition, the obtained culture supernatant liquid may be appropriately purified by column chromatography, ammonium sulfate fractionation, or the like to be used. In addition to the liquid form, the form of the obtained enzyme liquid may be formed into a powder form by spray drying or freeze-drying. At this time, a stabilizer or an excipient usually used may be added.

(Addition Amount of Metalloprotease)

The metalloprotease is preferably added in a range of 0.05 to 10.0 PU/g based on the total mass of raw material milk. The metalloprotease can be more preferably added in a range of 0.25 to 5.0 PU/g. This is because uneven in hardness inside a curd of a fermented milk product is reduced, and the texture becomes smooth within this range. In addition, by changing the addition amount, it is possible to change and adjust the hardness inside the curd. For example, even if 4.0 PU/g of the protease is added to raw material milk having a relatively high milk fat content (for example, more than 1.5% and 5.0% or less), the shape of the curd can be maintained. Therefore, the protease can be preferably used for a post-fermentation type fermented milk product. By adding 0.25 PU/g or more of the protease, more sufficient softness can be imparted to the curd. Meanwhile, by adding the protease in the present invention to low-fat milk or nonfat milk (for example, 1.5% or less), appropriate hardness can be imparted to the curd. That is, in order to obtain a fermented milk product having a desired hardness of a curd, it is possible to use the milk fat content contained in raw material milk and the addition amount of a *Paenibacillus*-derived protease as indices so as to determine the milk fat content and the addition amount of the protease, and so as to perform a fermentation step, {(for example, the addition amount is determined based on studies in advance performed by changing the addition amount of the protease with respect to raw material milk having a certain milk fat content (determine by preparing a calibration curve or the like)}.

The addition amount (enzyme amount) of the metalloprotease can be calculated as an enzyme activity per enzyme mass based on the enzyme amount 1.0 PU defined by the following means. To a 0.6% casein aqueous solution (pH 7.5, 2 mM calcium acetate-containing 50 mM tris-HCl buffer), 1 mL of an enzyme diluent is added, and a reaction is caused at 30° C. for 10 minutes. Thereafter, 5 mL of a trichloroacetic acid reagent (pH 4.0, 1.8% anhydrous sodium acetate, 1.8% trichloroacetic acid, 1.98% acetic acid) is added thereto to terminate the reaction. The resulting mixture is further allowed to stand at 30° C. for 30 minutes and filtered. Thereafter, the absorbance at 275 nm is measured. The amount of enzyme (enzyme activity) that releases an amino acid corresponding to 1 μg of tyrosine per minute under this condition is defined as 1 PU (Protease Unit).

<Lactic Acid Bacteria Starter>

The milk product according to the present invention may use a lactic acid bacteria starter in a method for manufacturing the milk product. In the present invention, the used type of lactic acid bacteria is not particularly limited. The present invention may use conventionally used lactic acid bacteria such as *Lactobacillus. delbrueckii* subsp. *bulgaricus, Streptococcus thermophilus, Lactobacillus casei*, and *Lactobacillus paracasei*. As a means of obtaining these lactic acid bacteria starters, commercially available products which are generally distributed can be purchased, or a strain which has been isolated independently can also be used. Incidentally, a plurality of lactic acid bacteria of the same type or of different types may be used in combination. In addition, probiotic bacteria such as *Lactobacillus bifidus* may be added and used simultaneously with the starter.

(Addition Amount of Lactic Acid Bacteria Starter)

The addition amount of the lactic acid bacteria starter is not particularly limited. A general amount can be added. For example, in the case of using a freeze-drying starter manufactured by Christian Hansen Holding A/S, the addition amount of the lactic acid bacteria starter may be 0.1 to 0.5 mg/g based on raw material milk. However, the addition amount is not particularly limited as long as being able to grow lactic acid bacteria.

<Raw Material Milk>

Raw material milk is not particularly limited but is a liquid or a solution of a powder, containing a milk component such as fresh milk, raw milk, whole milk, skimmed milk, whey, or butter. These can be used in combination.

The milk fat content contained in raw material milk is preferably 0 to 10% by mass. The milk fat content is more preferably 0.1 to 5.0% by mass, and still more preferably 1.0 to 5.0% by mass. In the presence of a neutral protease, the lower the milk fat content is, the higher the hardness of a fermented milk product tends to be. In the presence of a neutral protease, the higher the milk fat content is, the lower the hardness of a fermented milk product can be. The milk fat content contained in raw material milk varies depending on the type of milk but can be adjusted by adding butter or the like.

The nonfat milk solid content contained in raw material milk may be preferably 3.0 to 20% by mass.

If the nonfat milk solid content is less than the lower limit value or more than the upper limit value, the smoothness of a fermented milk product may be insufficient. If the nonfat milk solid content is less than the lower limit value, a fermented milk product is hardly solidified. If the nonfat milk solid content is more than the upper limit value, a fermented milk product may be extremely solidified. The milk product according to the present invention is not limited to a solid matter (for example, cheese) or a gel-like matter (for example, yoghurt), and includes a liquid matter and a sol-like matter (for example, a drink type yoghurt). In the case where the milk product is a liquid matter or a sol-like matter, the nonfat milk solid content may be less than the lower limit value (3.0%). The nonfat milk solid content includes a protein mainly containing casein, a saccharide mainly containing lactose, a salt mainly containing various inorganic salts, and the like.

A ratio between the milk fat content (% by mass) contained in raw material milk and the addition amount (PU/g) of a *Paenibacillus*-derived protease (the milk fat content: the addition amount of the protease) may be preferably 50:1 to 1:10 {that is, when the milk fat content (% by mass) is represented by "a" and the addition amount of the protease (PU/g) is represented by "b", a/b (% by mass g/PU) may be 50 to 0.1}. In addition, with regard to a change in hardness according to the value of the ratio and the addition amount of the protease, as the ratio is relatively higher, the hardness of a fermented milk product tends to be lowered (softened) by addition of the protease as compared with a fermented milk product without addition of the protease. Meanwhile, as the ratio is relatively lower, the hardness of a fermented milk product tends to be increased (hardened) by addition of the protease as compared with a fermented milk product without addition of the protease.

<Optional Components>

In the method for manufacturing a milk product according to the present invention, various components can be added, if necessary. Specific examples thereof include a metal salt contributing to stabilization of a milk product, various saccharides, ascorbic acid, glycerin or the like, starch as an excipient for improving ease of use, dextrin, an inorganic salt having a buffering action, lactose as a milk-derived component, whey, a milk protein, and a gelling agent such as agar, gelatin, pectin or the like.

(Lactase)

In the method for manufacturing a milk product according to the present invention, a lactase product such as a lactase solution can also be added. The lactase solution or the like is not particularly limited, and a commercially available product can be used.

(Another Enzyme)

In the method for manufacturing a milk product according to the present invention, it is possible to add various enzyme products, which are a liquid product, a powder product or the like. These enzyme products are not particularly limited. For example, one or more kinds selected from glucose isomerase, glucose oxidase, transglutaminase, lipase, cellulase, amylase, inulinase, and second protease can be used, and a commercially available product can be used.

The second protease includes proteases derived from microorganisms belonging to *Bacillus, Geobacillus, Aspergillus, Rhizopus, Rhizomucor*, and *Streptomyces*, a protease derived from lactic acid bacteria, and the like. Specifically, the protease may be preferably a protease derived from microorganisms selected from the group consisting of *Bacillus licheniformis, Bacillus subtilis, Bacillus amyloliquefaciens, Bacillus sp., Geoacillus caldoproteolyticus, Aspergillus sp., Aspergillus oryzae, Aspergillus melleus, Lactobacillus helveticus, Lactobacillus bulgaricus*, and *Streptococcus thermophilus*.

<<Properties of Milk Product>>

<Evaluation of Texture>

Evaluation of the texture (smoothness and/or viscosity) and the hardness of the fermented milk product according to the present invention (break strength analysis) can be made based on physical property values measured by using a creep meter (RE2-33005C) manufactured by Yamaden Co., Ltd.

(Smoothness)

As for "smoothness" in the texture, evaluation can be made based on linearity of a waveform measured by the creep meter. When there are fewer disturbances in a waveform (closer to a straight line), it can be said that the texture is smoother.

(Viscosity)

As for viscosity (stringiness: texture analysis), evaluation can be made based on visual observation and based on an inclination of a tangent when a plunger rises as described below. It is considered that if the inclination of the tangent is smaller, the fermented milk product is more viscous, has more richness, and a feeling of further gathering in the mouth can be imparted to the fermented milk product.

(Hardness)

The hardness of a curd of the fermented milk product according to the present invention can be evaluated by break strength analysis as described below. As a specific physical property value, when a plunger is pushed down with a creep meter so as not to break a curd, a load (N) at the time when the curd is broken is defined as a "breaking point" (value automatically calculated by the creep meter), and the hardness thereof can be evaluated. The hardness of the fermented milk product according to the present invention can be adjusted to a desired hardness and is not particularly limited. However, the hardness (breaking point) may be preferably 0.002 to 1.0 N, and more preferably 0.005 to 0.5 N.

(Change in SDS-PAGE of Protein by Fermentation)

In a case where raw material milk containing the metalloprotease in the present invention is fermented, it may be preferable to minimize a change in a milk protein other than κ-casein between before and after fermentation. This is because the texture can be improved without changing a taste, a flavor, and the like. This can be confirmed by subjecting a fermented product before and after fermentation to SDS-PAGE and observing a change in each band.

Here, the ratio of each band fraction can be calculated by drying a gel which has been subjected to SDS-PAGE electrophoresis, then taking a grayscale image of the gel with a scanner GT-X820 manufactured by EPSON Co., Ltd., and measuring the concentration (amount of protein) of each band with an ImageJ software (NIH, Bethesda, Md.).

In the present invention, it is preferable that a band fraction other than a band fraction of about 25 kDa by SDS-PAGE electrophoresis does not fluctuate largely between before and after fermentation. The fermentation is performed at 20 to 60° C. for five hours after the metalloprotease of the present invention is added to raw material milk. With such characteristics, it is estimated that other original flavors and the like can be prevented from being impaired by an enzyme treatment while the curd hardness, the smoothness, and the like of the fermented milk product are adjusted. Note that the molecular weight of each band by SDS-PAGE electrophoresis can be calculated by a known means and that a range of the molecular weight in each band area can be similarly calculated by a known means.

<<Method for Manufacturing Milk Product>>

The method for manufacturing a milk product according to the present invention is not particularly limited. The method may include a first step of mixing raw material milk and lactic acid bacteria to obtain a mixed liquid, a second step of fermenting the mixed liquid, and a step of adding a *Paenibacillus*-derived protease to the raw material milk and/or the mixed liquid (protease addition step). The first step and the second step is sequentially performed and the protease addition step is performed before the second step is completed. For example, in a case where the milk product is fermented milk, the method for manufacturing the fermented milk may include (1) a step of simultaneously adding a lactic acid bacteria starter and a metalloprotease to milk at a predetermined concentration, (2) a step of stirring the resulting mixture at 43° C. for about 10 to about 15 minutes, (3) a step of dispensing the resulting mixed liquid into a glass container and fermenting the mixed liquid at 43° C. for five hours, (4) a step of keeping the obtained fermentation preparation refrigerated at 4 to 5° C. for one day or more, and the like.

<<Applications of Milk Product>>

The pre-fermentation type can be suitable for a drink type, a fruit yoghurt, and the like. The post-fermentation type can be suitable for a plain yoghurt and the like. In addition, any types can be formed into a milk product with lactase added because of having no influence on the activity of lactase.

EXAMPLES

Hereinafter, the present invention will be described with reference to Examples and Comparative Examples, but the present invention is not limited to Examples and Comparative Examples.

Manufacture of Fermented Milk Product

Manufacture Example 1

(Material)

Milk: Meiji Oishii Gyunyu (Tasty milk) (milk fat content 3.8±0.3% by mass, nonfat milk solid content 8.6±0.3% by mass)

Neutral protease: A *Paenibacillus polymyxa* NBRC 15309 strain was inoculated into a Nutrient liquid medium manufactured by Difco Laboratories Inc. and cultured at 30° C. for two days. 10,000 g of the resulting culture broth was centrifuged for 10 minutes, and the resulting supernatant was desalted by dialysis to be used. Note that the protease had the above-described properties (a) to (g).

Lactic acid bacteria starter: lactic acid bacteria powder FD-DVS YF-L812 Yo-Flex (manufactured by Christian Hansen Holding A/S, a mixture of *Lactobacillus. delbrueckii* subsp. and *Streptococcus. thermophilus*).

(Manufacturing Method)

450 g of milk was put in a sterilized glass container, and a lactic acid bacteria starter YF-L812 and a neutral protease were simultaneously added thereto. The addition concentration of the starter was 0.1 mg/g, and the addition concentration of the neutral protease was 1.0 (PU/g) based on the raw material milk. The milk containing the starter and the neutral protease was stirred in a thermostatic water bath at 43° C. for about 10 to about 15 minutes. Subsequently, the milk was dispensed into a glass container (manufactured by Daiso, 220 ml) and fermented at 43° C. for five hours. The fermented preparation was kept refrigerated (4 to 5° C.) for one day or more to obtain a yoghurt of Manufacture Example 1.

Manufacture Example 2

A yoghurt of Manufacture Example 2 was obtained in the same manner as Manufacture Example 1 except that FD-DVS YC-380 Yo-Flex (manufactured by Christian Hansen Holding A/S, a mixture of *Lactobacillus. delbrueckii* subsp. and *Streptococcus. thermophilus*) was used as the lactic acid bacteria starter.

Manufacture Example 3

A yoghurt of Manufacture Example 3 was obtained in the same manner as Manufacture Example 1 except that low-fat milk (UHT sterilized milk: Meiji Oishii Gyunyu low fat, milk fat content 1.2% by mass, milk solid content 11±1.0% by mass) was used as the milk.

Manufacture Example 4

A yoghurt of Manufacture Example 4 was obtained in the same manner as Manufacture Example 1 except that nonfat milk (UHT sterilized milk: nonfat milk manufactured by Koiwai Dairy Products CO., LTD, milk fat content 0.1% by mass, milk solid content 8.8±0.2% by mass) was used as the milk.

Manufacture Example 5

A yoghurt of Manufacture Example 5 was obtained in the same manner as Manufacture Example 1 except that no neutral protease was added.

Manufacture Example 6

A yoghurt of Manufacture Example 6 was obtained in the same manner as Manufacture Example 2 except that no neutral protease was added.

Manufacture Example 7

A yoghurt of Manufacture Example 7 was obtained in the same manner as Manufacture Example 3 except that no neutral protease was added.

Manufacture Example 8

A yoghurt of Manufacture Example 8 was obtained in the same manner as Manufacture Example 4 except that no neutral protease was added.

Evaluation

Test Example 1 (Evaluation of Physical Properties on Texture)

(Break Strength Analysis)

Figure 1:
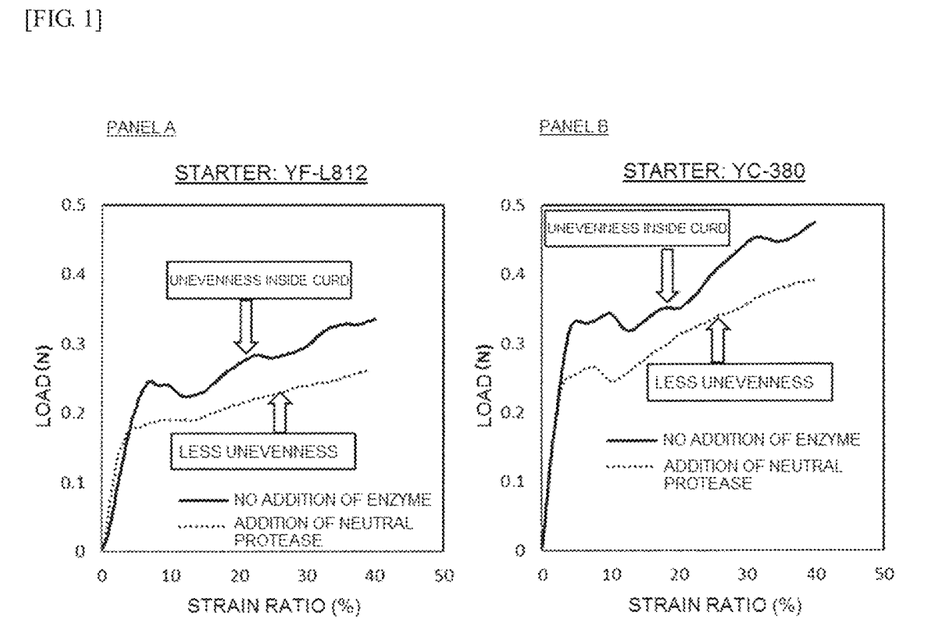

Physical properties of the yoghurts of Manufacture Examples 1 and 2 (Examples) and the yoghurts of Manufacture Examples 5 and 6 (Comparative Examples) were measured. Physical properties were measured by using a creep meter (RE2-33005C) manufactured by Yamaden Co., Ltd. Break strength analysis was performed without breaking a curd. FIG. 1 illustrates results thereof. In the break strength analysis, the press-in speed of a plunger was set to 1 mm/s, the thickness of a sample was set to 47 mm, the shape of the plunger was set to a round shape with a diameter of 16 mm, a measurement strain ratio was set to 40%, and a load cell standard was set to 2 N.

As shown in FIG. 1, addition of a neutral protease reduces the hardness of a curd. It is found that there is unevenness in the hardness inside the curd (uneven waveform of the solid line) in a case of no addition of an enzyme. Meanwhile, addition of a neutral protease reduces unevenness in the hardness inside the curd (waveform of the dotted line), and it is understood that the texture becomes smooth.

(Texture Analysis)

Figure 2:
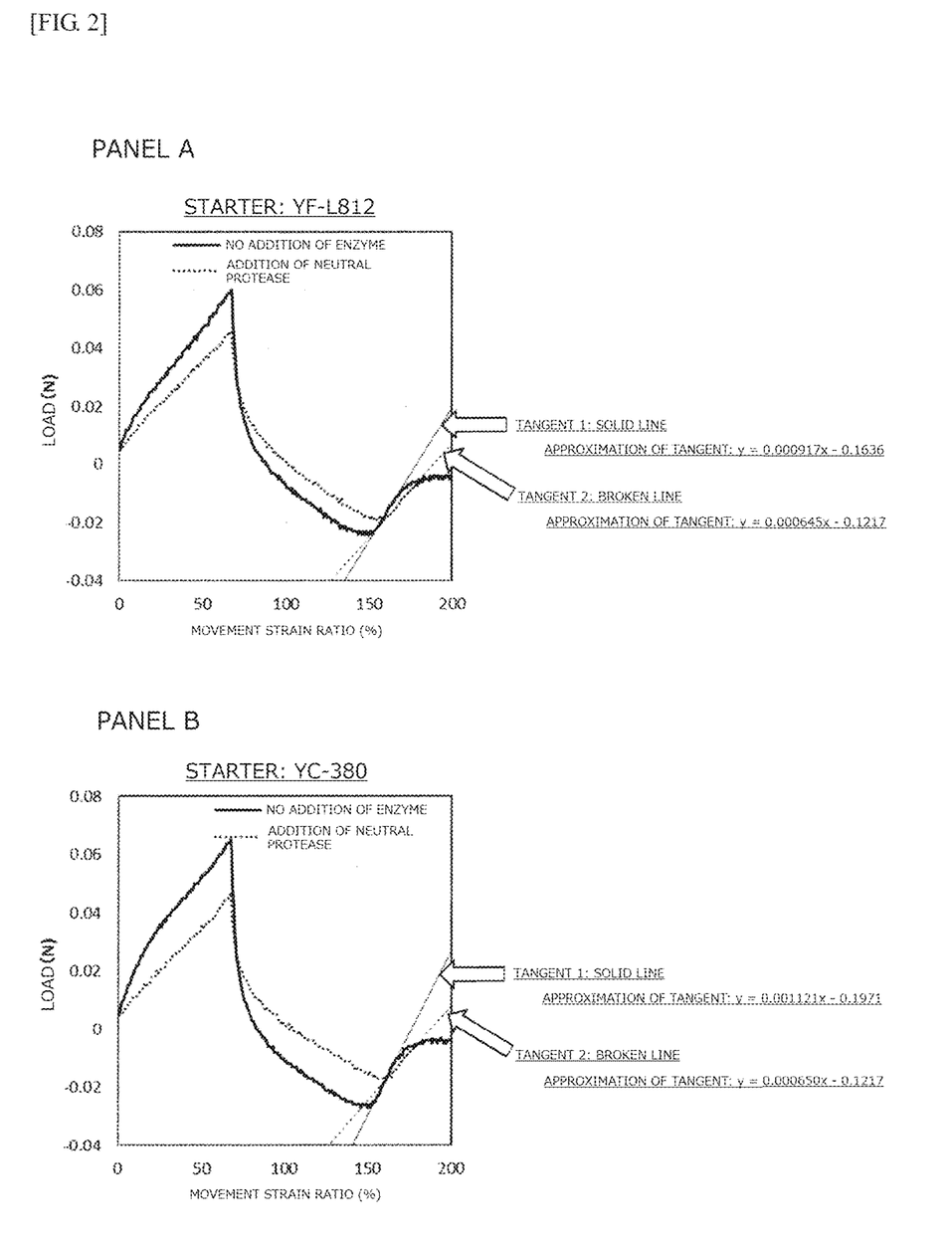

Texture analysis was performed by stirring a sample sufficiently with a spoon to break a curd and putting the sample in a dedicated cup. In the texture analysis, the press-in speed of a plunger was set to 5 mm/s, the thickness of a sample was set to 15 mm, the shape of the plunger was set to a round shape with a diameter of 16 mm, a measurement strain ratio was set to 66.66%, and a load cell standard was set to 2 N. With this setting, in the texture analysis, the plunger was inserted into the curd by 10 mm, subsequently the plunger was raised, and a change in load on the plunger was measured. FIG. 2 illustrates results thereof. The load increased by the insertion of the plunger showed a negative value as the plunger was raised. When the plunger was separated from an interface of the curd, stringiness occurred. In a case of addition of a neutral protease, adhesion (area having a load of zero or less) decreased as compared with a case of no addition of an enzyme, but stringiness-like viscosity increased. With regard to the stringiness-like viscosity, when the plunger is raised, a pulling force functions in the opposite direction, and therefore the rise of the load is gentle. When a tangent is drawn to a waveform, the inclination of a tangent (tangents 2 and 4, broken lines) in the case of addition of a neutral protease is smaller than the inclination of a tangent (tangents 1 and 3, solid lines) in the case of no addition of an enzyme. The inclination of the tangent was determined using Excel (registered trademark) as follows. An approximate straight line was drawn in a range of a strain ratio of 14% from a point where the load of the waveform was the minimum, and the inclination of the tangent was determined from the obtained approximate straight line. Table 1 illustrates details thereof. Because of this viscosity, there was a feeling of gathering in the mouth as a texture, and the texture became rich and smooth.

TABLE 1

|  | Inclination of tangent |
|---|---|
| Manufacture Example 1 (Example) | 0.000645 |
| Manufacture Example 5 (Comparative Example) | 0.000917 |
| Manufacture Example 2 (Example) | 0.000650 |
| Manufacture Example 6 (Comparative Example) | 0.001121 |

Test Example 2 (Evaluation of Physical Properties on Texture in Low-Fat Milk)

(Break Strength Analysis)

Figure 3:
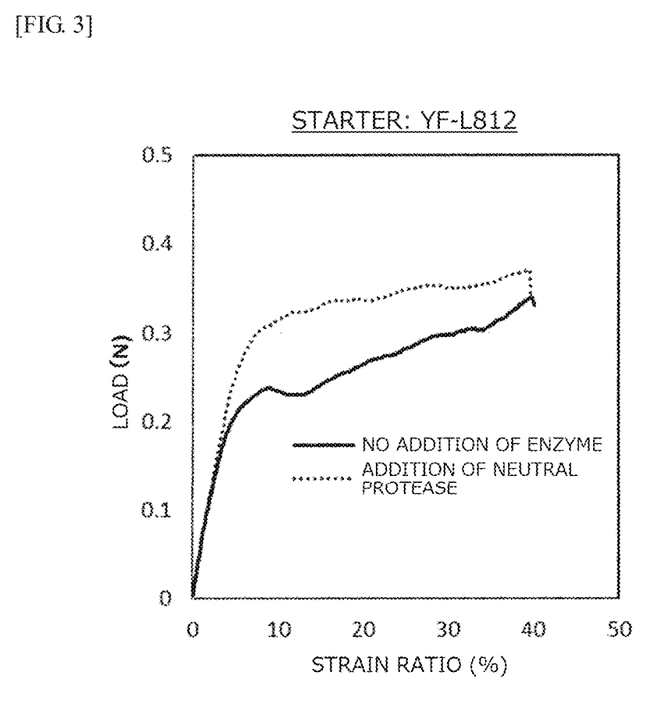
FIG. 3 is a graph showing results of break strength analysis by a creep meter for yoghurts of Manufacture Examples 3 and 7.

For yoghurts of Manufacture Example 3 (Example) and Manufacture Example 7 (Comparative Example), break strength analysis was performed in the same manner as Test Example 1. FIG. 3 illustrates results thereof.

As shown in FIG. 3, addition of a neutral protease increased the hardness of a curd. It is found that there is unevenness in the hardness inside the curd (uneven waveform of the solid line) in a case of no addition of an enzyme (Manufacture Example 7). Meanwhile, addition of a neutral protease reduces unevenness in the hardness inside the curd (waveform of the dotted line), and it is understood that the texture becomes smooth.

(Texture Analysis)

Figure 4:
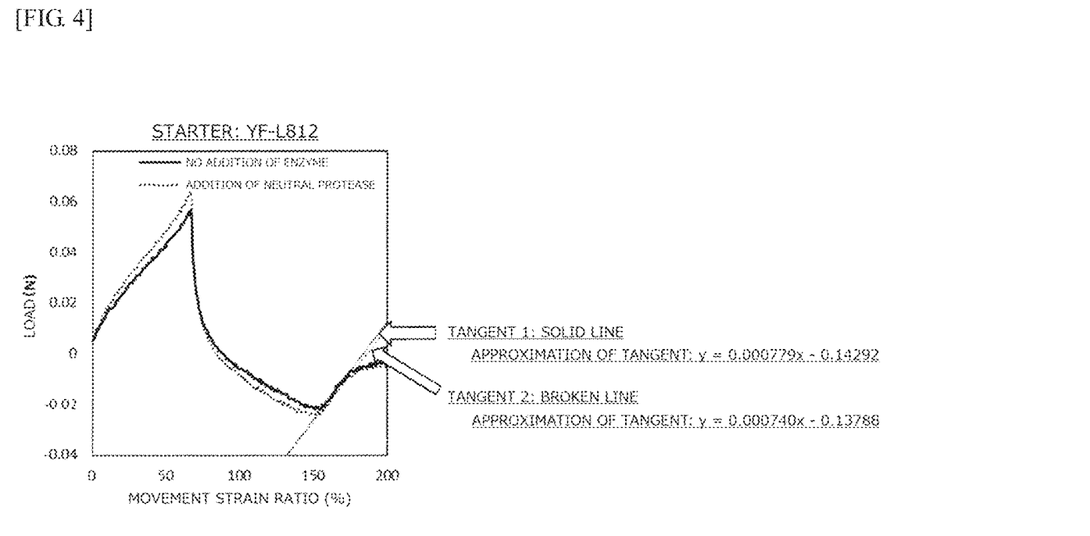
FIG. 4 is a graph showing results of texture analysis by a creep meter for yoghurts of Manufacture Examples 3 and 7.

Texture analysis was performed in the same manner as Test Example 1. FIG. 4 illustrates results thereof. In a case of addition of a neutral protease, adhesion (area having a load of zero or less) increased as compared with a case of no addition of an enzyme. Furthermore, although not illustrated in Tables, the inclination of the tangent decreased, and the stringiness-like viscosity increased. Because of this viscosity, there was a feeling of gathering in the mouth as a texture, and the texture became rich and smooth.

Test Example 3 (Evaluation of Physical Properties on Texture in Nonfat Milk)

(Break Strength Analysis)

Figure 5:
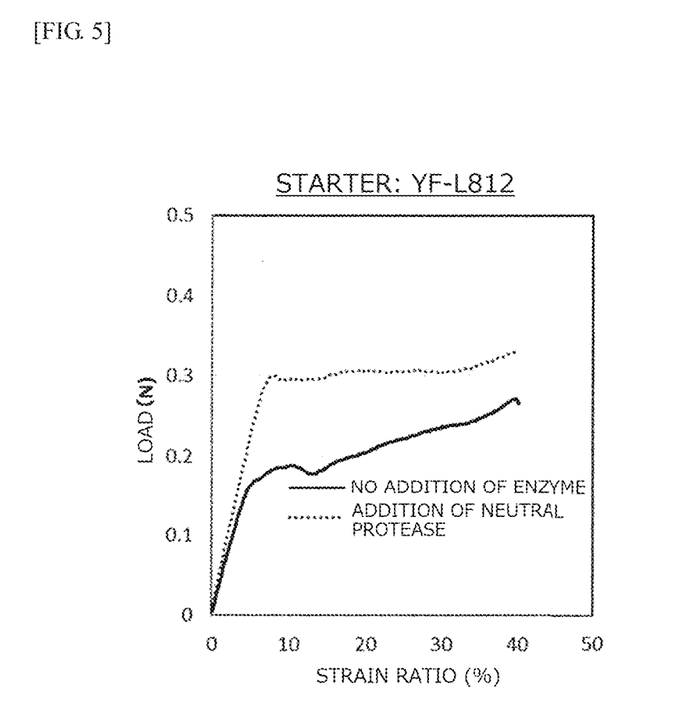
FIG. 5 is a graph showing results of break strength analysis by a creep meter for yoghurts of Manufacture Examples 4 and 8.

For yoghurts of Manufacture Example 4 (Example) and Manufacture Example 8 (Comparative Example), break strength analysis was performed in the same manner as Test Example 1. FIG. 5 illustrates results thereof.

As shown in FIG. 5, addition of a neutral protease increased the hardness of a curd. It is found that there is unevenness in the hardness inside the curd (uneven waveform of the solid line) in a case of no addition of an enzyme (Manufacture Example 8). Meanwhile, addition of a neutral protease reduces unevenness in the hardness inside the curd (waveform of the dotted line), and it is understood that the texture becomes smooth.

(Texture Analysis)

Figure 6:
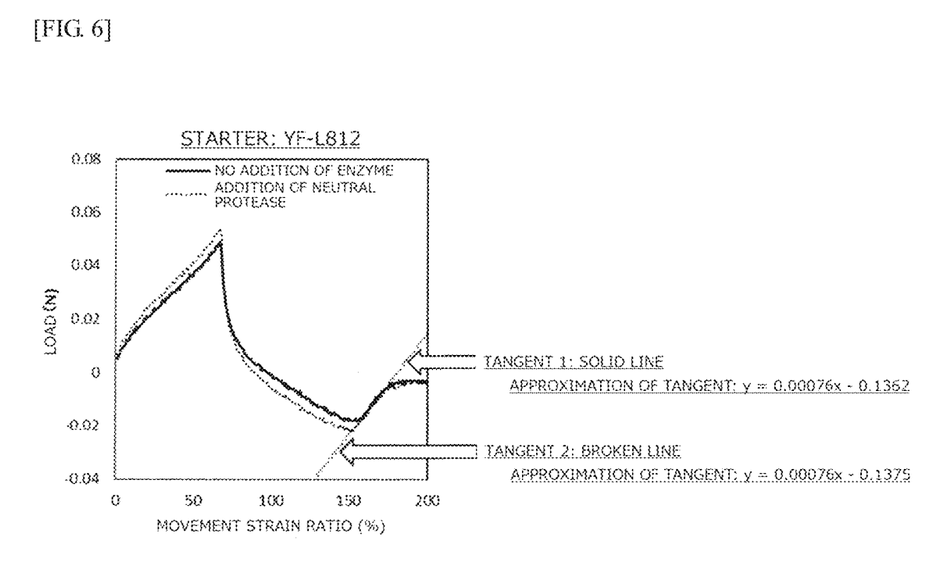
FIG. 6 is a graph showing results of texture analysis by a creep meter for yoghurts of Manufacture Examples 4 and 8.

Texture analysis was performed in the same manner as Test Example 1. FIG. 6 illustrates results thereof. In a case of addition of a neutral protease, adhesion (area having a load of zero or less) increased as compared with a case of no addition of an enzyme (Manufacture Example 8). Although not illustrated in Tables, the inclination of the tangent hardly changed. However, as a result of the sensory evaluation, an increase in hardness and adhesion brought a feeling of gathering in the mouth as a texture and made the texture rich and smooth.

Test Example 4 (Concentration Dependency)

Figure 7:
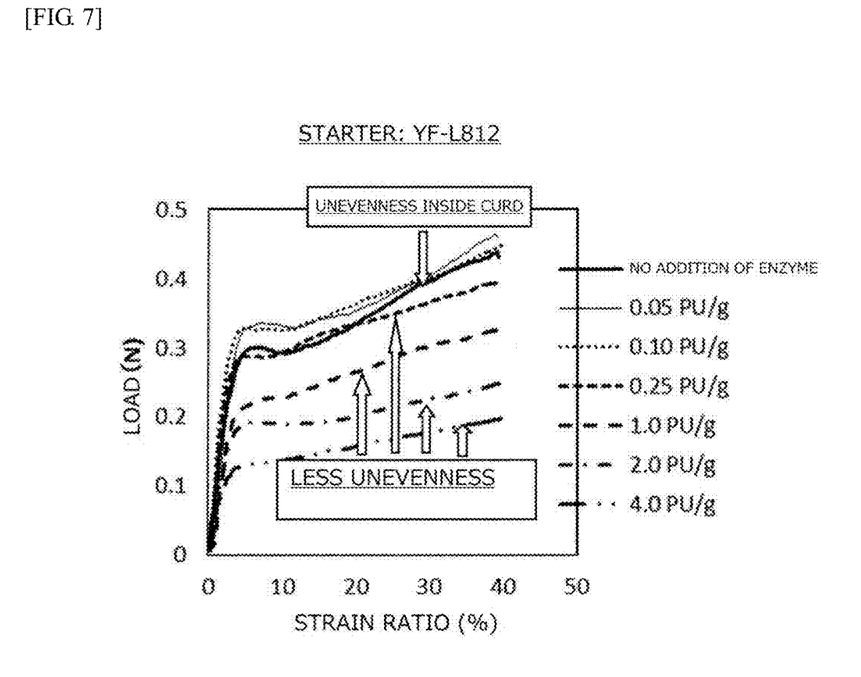
FIG. 7 is a graph showing results of break strength analysis by a creep meter in a case where the addition amount of an enzyme is changed.

The addition concentration of the neutral metalloprotease having a texture modification effect in the present invention was changed (0.05, 0.10, 0.25, 1.0, 2.0 and 4.0 PU/g) with regard to the fermented milk of Manufacture Example 1 on the purpose of study. Break strength analysis was performed without breaking a curd. FIG. 7 illustrates results thereof. Addition of 0.25 PU/g or more of the neutral protease reduced the hardness of a curd. Even if 4.0 PU/g of the neutral protease was added, the shape of the curd was maintained, and it was considered that this sample could be used for post-fermentation type fermented milk. In a case of no addition of an enzyme, there is unevenness in the hardness inside the curd (uneven waveform of the bold solid line). However, addition of 0.05 PU/g or more of the neutral protease reduces the unevenness in the hardness inside the curd, and it is understood that the texture becomes smooth.

Test Example 5 (Sensory Test on Texture)

10 subjects were subjected to a sensory test for the yoghurt with addition of a neutral protease (Manufacture Example 1) and the yoghurt without addition of a neutral protease (Manufacture Example 5) based on the following evaluation criteria in the following four criteria. Table 2 indicates results thereof.

(Evaluation Criteria)

As evaluation criteria, the texture of a yoghurt was divided into four evaluation items of smoothness, mouthfeel, flavor, and richness. Evaluation was performed in four stages (very good=3 points, good=2 points, normal=1 point, bad=0 point), and an average point (○=2 to 3 points, Δ=1 to 2 points, x=0 to 1 point) was calculated.

TABLE 2

|  | Smoothness | Mouthfeel | Flavor | Richness |
|---|---|---|---|---|
| Manufacture Example 1 (addition) | ○ | ○ | ○ | ○ |
| Manufacture Example 5 (no addition) | Δ | Δ | ○ | x |

Test Example 6 (Change in Band in SDS-PAGE Between Before and After Fermentation)

(Fermentation Method)

In a similar manner to Manufacture Example 1, the addition concentration of the neutral protease was 1.0 PU/g, and a sample was stirred at 43° C. for 10 to 15 minutes. Thereafter, the sample was dispensed into a 15 mL centrifuge tube and fermented at 43° C. for five hours. For the fermentation liquid before the fermentation and 1, 2, 3, 4, and 5 hours after the fermentation, a change in protein in the fermentation process was analyzed by SDS-polyacrylamide gel electrophoresis according to the following manner.

(SDS-Polyacrylamide Gel Electrophoresis)

Figure 8:
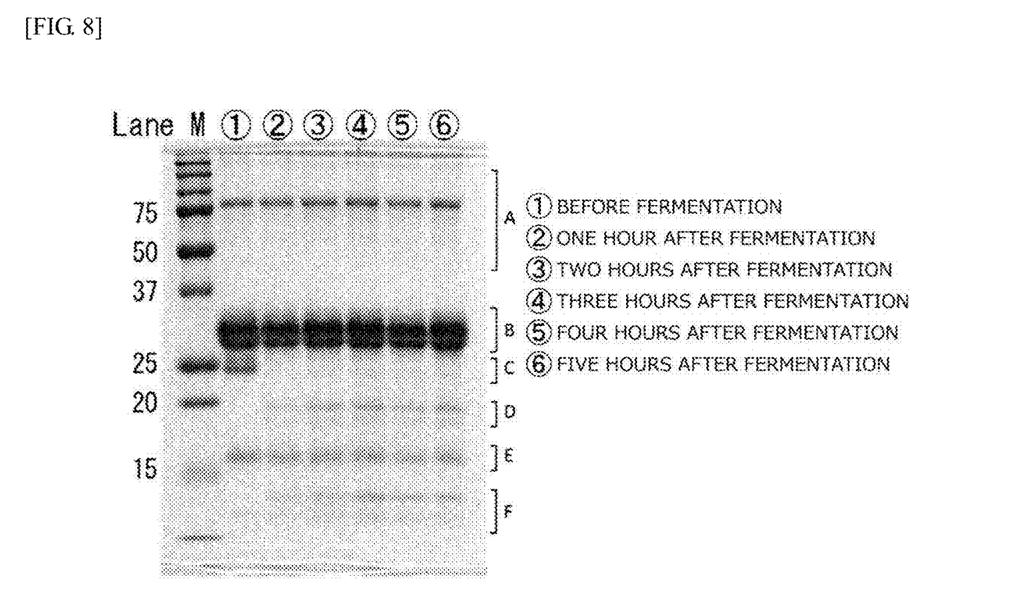
FIG. 8 is a diagram showing a change with time in SDS-polyacrylamide gel electrophoresis with respect to fermentation time in a fermentation reaction by the protease of the present invention.

The obtained fermentation liquid was diluted with ultrapure water by 20 times. The dilution was mixed with Sample Buffer for SDS-PAGE (0.125 M tris-HCl pH 6.8, 0.0125% bromothymol blue, 20% glycerin, 2.5% SDS, 2.5% 2-mercaptoethanol) at a ratio of 1:1 and then subjected to a heat treatment at 95° C. for five minutes to prepare an electrophoresis sample. A molecular weight marker and the electrophoresis sample were set out onto a 12.5% acrylamide gel (4% stacking gel, gel thickness 1 mm, electrophoresis distance 50 mm), and electrophoresis was performed in a Marisol industrial electrophoresis tank at a stacking constant current of 10 mA at a separating current of 20 mA until an electrophoresis front line reached the vicinity of a gel lower end. BIO-RAD #161-0313 (Prestained) was used for the molecular weight marker (lane M). The gel after the electrophoresis was subjected to protein staining with a CBB stain liquid (APRO SP-4010) for one hour. FIG. 8 illustrates results of the electrophoresis. Table 3 illustrates band analysis results by ImageJ.

Note that band area A (100 to 40 kDa), band area B (33 to 26 kDa), band area C (26 to 23 kDa), band area D (20 to 18 kDa), band area E (16.5 to 15 kDa), and band area F (14 to 10 kDa) in the band analysis results by ImageJ illustrated in Table 3 respectively correspond to bands represented by A to F in FIG. 8 illustrating the electrophoresis results.

TABLE 3

| Band area | Lane ① | ② | ③ | ④ | ⑤ | ⑥ |
|---|---|---|---|---|---|---|
| A | 10.9 | 12.6 | 13.4 | 13.3 | 12.5 | 13.6 |
| B | 64.5 | 73.7 | 71.9 | 71.0 | 72.9 | 70.9 |
| C | 15.8 | 0.9 | 1.1 | 1.0 | 1.1 | 1.3 |
| D |  | 2.3 | 3.9 | 4.3 | 3.7 | 4.6 |
| E | 7.5 | 6.7 | 5.4 | 5.4 | 5.4 | 5.2 |
| F | 1.2 | 3.8 | 4.2 | 5.1 | 4.4 | 4.5 |
| D + F | 1.2 | 6.1 | 8.1 | 9.3 | 8.1 | 9.1 |

From one hour after start of the fermentation, a band of κ-casein {about 25 kDa (band area C)} specifically disappeared, and the bands in the band areas D and F increased. From two hours after the start of the fermentation, the concentration in each band area was not largely changed, and the concentration of another milk-derived protein did not change largely even five hours after the start of the fermentation. Therefore, according to the manufacturing method of the present invention, it is deduced that a texture of milk can be improved without largely changing the properties of the milk except for the texture.

Test Example 7 (Change in Protease Activity with Change in pH)

Figure 9:
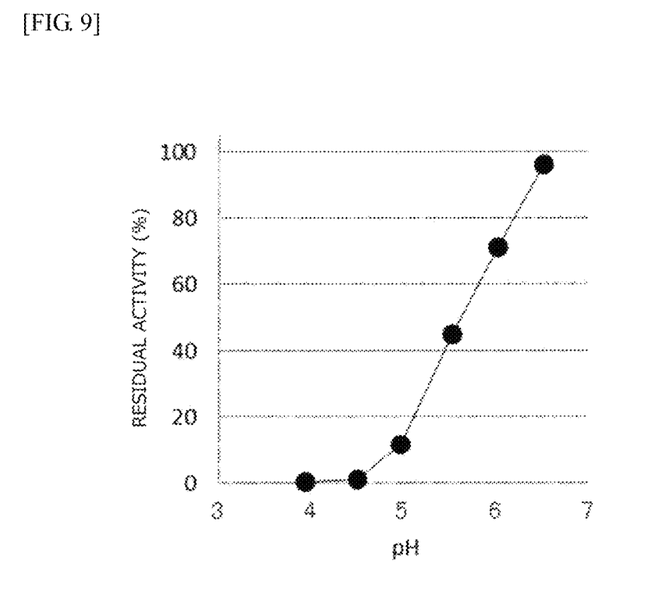
FIG. 9 is a graph showing results of pH dependency of a preferable protease in the present invention.

A pH stability test of a neutral protease was performed. A neutral protease was diluted with 50 mM MES containing 1 mM Ca acetate (pH 6.5) to about 1,000 PU/mL. After the dilution, pH was adjusted with 1 N hydrochloric acid, and the diluted solution was heated at 43° C. for one hour. The protease was measured to determine residual activity thereof when a sample the pH of which had not been adjusted and which had not been heated had activity of 100%. Protease activity was measured as follows. Azocasein (SIGMA A2765) was dissolved in 50 mM MES containing 1 mM Ca acetate (pH 6.5) so as to have a concentration of 5%, and the resulting solution was used as a substrate. 300 µL of 50 mM MES containing 1 mM Ca acetate (pH 6.5) and 100 µL of a diluted enzyme liquid were added to 100 µL of 5% Azocasein. A reaction was caused at 43° C. for 30 minutes, and then the reaction was terminated with 500 µL of 10% trichloroacetic acid. An equal amount of 1 N NaOH was added to the centrifugation supernatant and mixed therewith, and the absorbance at OD 428 nm was measured. FIG. 9 illustrates results thereof. At 43° C. of a general fermentation temperature of fermented milk, the neutral protease was inactivated in one hour at a pH of 4.5. Therefore, it is estimated that the neutral protease activity does not remain in the fermentation preparation, and the neutral protease does not adversely affect the fermentation preparation during storage.

Test Example 8 (Combination Use of Neutral Protease and Lactase Solution)

Figure 10:
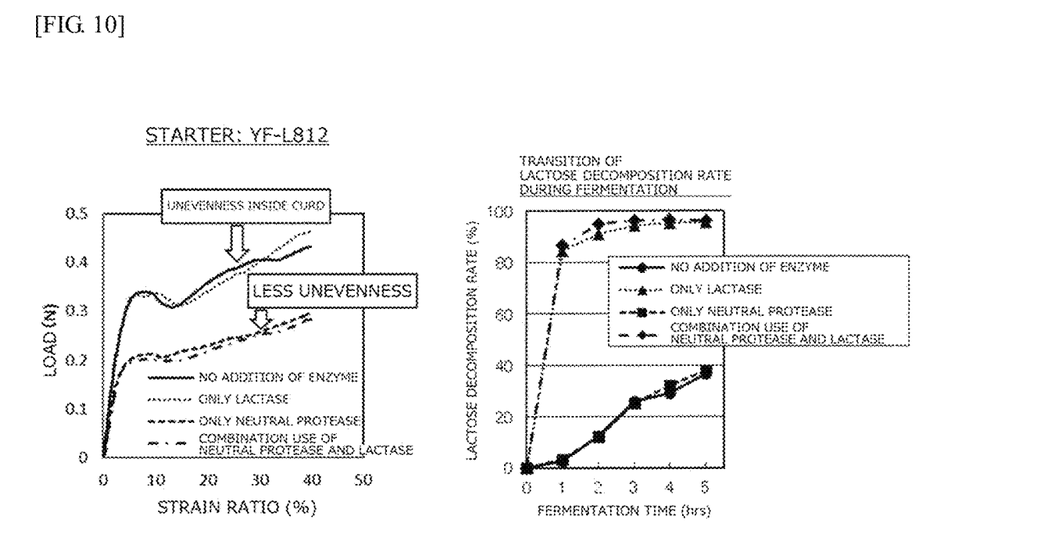
FIG. 10 is graphs showing results of break strength analysis by a creep meter and a lactose decomposition rate in a case where a preferable protease in the present invention and a lactase are used in combination.

For combination use of a neutral protease and a lactase solution, a change in texture and an influence on a lactose decomposition rate by lactase were studied. In a similar manner to Manufacture Example 1, a yoghurt was manufactured with a starter addition concentration of 0.1 mg/g and a neutral protease addition concentration of 1 PU/g. Softness and unevenness inside a curd (smoothness) were studied in a similar manner to the above-described break strength analysis. Panel A of FIG. 10 illustrates results thereof. Incidentally, the milk containing the starter and the neutral protease was stirred at 43° C. for about 10 to about 15 minutes, then dispensed into a glass container, and fermented at 43° C. for five hours. The fermented preparation was kept refrigerated for one day or more, and physical properties thereof were measured. Break strength analysis was performed without breaking a curd. Panel B of FIG. 10 illustrates results thereof.

Despite being a protease, the neutral protease did not cancel out an effect of lactase when being added simultaneously with lactase, and thus it is expected to cause a lactose intolerance prevention effect and a sweet taste improving effect due to lactose decomposition. Meanwhile, lactase did not cancel out an effect of the neutral protease, either. Therefore, it is expected that smooth fermented milk can be manufactured.

The invention claimed is:
1. A method for manufacturing a yoghurt product, comprising:
mixing raw material milk and lactic acid bacteria to obtain a mixed liquid,
fermenting the mixed liquid until yoghurt is obtained, and
adding a *Paenibacillus*-derived protease to the raw material milk and/or the mixed liquid before the fermentation of the mixed liquid is completed, wherein the *Paenibacillus*-derived protease is added in an amount of 0.05 to 10.0 PU/g based on a total mass of the raw material milk.
2. The method according to claim 1, wherein a ratio of the milk fat content (% by mass) contained in the raw material milk to the added amount (PU/g) of the protease (the milk fat content:the addition amount of the protease) is 50:1 to 1:10.
3. The method according to claim 1, wherein the milk fat content contained in the raw material milk is 0 to 10% by mass.
4. The method according to claim 1, wherein a nonfat milk solid content contained in the raw material milk is 3.0 to 20% by mass.
5. The method according to claim 1, wherein the *Paenibacillus*-derived protease has the following properties (1) to (5),
(1) the protease is produced by bacteria belonging to *Paenibacillus*,
(2) the protease degrades κ-casein and hemoglobin in a neutral pH range,
(3) the protease is stable at a pH of 5.5 to 9.0 and has an optimum pH of 7.0 to 8.0,
(4) the protease acts at 20 to 75° C. and has an optimum temperature of 50 to 60° C., and
(5) the protease is estimated to have a molecular weight by SDS polyacrylamide gel electrophoresis of 32,000 to 34,000 Da.
6. The method according to claim 1, further comprising adding one or more selected from the group consisting of lactase, glucose isomerase, glucose oxidase, transglutaminase, lipase, cellulase, amylase, inulinase, laccase, peroxidase, and a second protease other than the *Paenibacillus*-derived protease to the raw material milk and/or the mixed liquid.
7. A yoghurt product produced by the method of claim 1, wherein a breaking point of a curd as measured using a creep meter is 0.002 to 1.0 N.
8. The method according to claim 1, wherein the *Paenibacillus*-derived protease is a protease derived from microorganisms selected from the group consisting of *Paenibacillus polymyxa, Paenibacillus macerans, Paenibacillus pabuli, Paenibacillus peoriae, Paenibacillus thiaminolyticus, Paenibacillus validus, Paenibacillus glucanolyticus, Paenibacillus kobensis, Paenibacillus lautus, Paenibacillus alginolyticus, Paenibacillus alvei, Paenibacillus amylolyticus, Paenibacillus chitinolyticus, Paenibacillus chondroitinus, Paenibacillus curdlanolyticus, Paenibacillus durus, Paenibacillus ehimensis*, and *Paenibacillus* sp.
9. The method according to claim 1, wherein the *Paenibacillus*-derived protease is a protease derived from *Paenibacillus polymyxa* or microorganisms belonging to *Paenibacillus* in which homology of 16S rDNA is 98% or more as compared with the sequence of *Paenibacillus polymyxa*.
10. The method according to claim 1, wherein the *Paenibacillus*-derived protease is a protease derived from *Paenibacillus polymyxa*.
11. The method according to claim 5, wherein the protease hardly exhibits a proteolytic action on α-casein or β-casein in a neutral pH range.
12. The method according to claim 6, wherein the second protease is a protease derived from microorganisms belonging to *Bacillus, Geobacillus, Aspergillus, Rhizopus, Rhizomucor, Streptomyces*, or lactic acid bacteria.

13. The method according to claim 6, wherein the second protease is a protease derived from microorganisms selected from the group consisting of *Bacillus licheniformis, Bacillus subtilis, Bacillus amyloliquefaciens, Bacillus* sp., *Geoacillus caldoproteolyticus, Aspergillus* sp., *Aspergillus oryzae, Aspergillus melleus, Lactobacillus helveticus, Lactobacillus bulgaricus,* and *Streptococcus thermophilus.*

* * * * *